US012797431B2

(12) United States Patent
Feng et al.

(10) Patent No.: US 12,797,431 B2
(45) Date of Patent: Nov. 17, 2026

(54) TRADITIONAL CHINESE MEDICINE FERMENTED PREPARATION FOR PREVENTING AND TREATING GOUT, ITS PREPARATION METHOD AND APPLICATION

(71) Applicant: Henan University of Chinese Medicine, Zhengzhou (CN)

(72) Inventors: Shuying Feng, Luoyang (CN); Baiyan Wang, Zhengzhou (CN); Aifang Li, Zhengzhou (CN); Qianqian Wang, Zhengzhou (CN); Dandan Guo, Zhengzhou (CN); Yu Huang, Zhengzhou (CN); Wei Chen, Zhengzhou (CN); Wei Fan, Kaifeng (CN)

(73) Assignee: Henan University of Chinese Medicine, Zhengzhou (CN)

( * ) Notice: Subject to any disclaimer, the term of this patent is extended or adjusted under 35 U.S.C. 154(b) by 288 days.

(21) Appl. No.: 18/740,537

(22) Filed: Jun. 12, 2024

(65) Prior Publication Data

US 2024/0415915 A1 Dec. 19, 2024

(30) Foreign Application Priority Data

Jun. 13, 2023 (CN) ......................... 202310697717.5

(51) Int. Cl.

| | |
|---|---|
| ***A61K 36/714*** | (2006.01) |
| ***A61K 9/00*** | (2006.01) |
| ***A61K 9/19*** | (2006.01) |
| ***A61K 33/06*** | (2006.01) |
| ***A61K 35/00*** | (2006.01) |
| ***A61K 35/747*** | (2015.01) |
| ***A61K 36/06*** | (2006.01) |
| ***A61K 36/17*** | (2006.01) |
| ***A61K 36/238*** | (2006.01) |
| ***A61K 36/284*** | (2006.01) |
| ***A61K 36/484*** | (2006.01) |
| ***A61K 36/54*** | (2006.01) |
| ***A61K 36/65*** | (2006.01) |
| ***A61K 36/88*** | (2006.01) |
| ***A61K 36/8994*** | (2006.01) |
| ***A61K 36/90*** | (2006.01) |
| ***A61P 19/06*** | (2006.01) |

(52) U.S. Cl.

CPC .......... *A61K 36/714* (2013.01); *A61K 9/0053* (2013.01); *A61K 9/19* (2013.01); *A61K 33/06* (2013.01); *A61K 35/747* (2013.01); *A61K 36/06* (2013.01); *A61K 36/17* (2013.01); *A61K 36/238* (2013.01); *A61K 36/284* (2013.01); *A61K 36/484* (2013.01); *A61K 36/54* (2013.01); *A61K 36/65* (2013.01); *A61K 36/88* (2013.01); *A61K 36/8994* (2013.01); *A61K 36/90* (2013.01); *A61P 19/06* (2018.01); *A61K 2035/115* (2013.01); *A61K 2236/19* (2013.01)

(58) Field of Classification Search

CPC ...... A61K 36/714; A61K 9/0053; A61K 9/19; A61K 33/06; A61K 35/747; A61K 36/06; A61K 36/17; A61K 36/238; A61K 36/284; A61K 36/484; A61K 36/54; A61K 36/65; A61K 36/88; A61K 36/8994; A61K 36/90; A61K 2035/115; A61K 2236/19; A61K 36/8964; A61K 9/0095; A61K 9/06; A61K 9/16; A61K 9/48; A61K 9/7023; A61K 36/064; A61K 36/71; A61K 36/896; A61P 19/06; Y02A 50/30; A23L 2/382; A23L 2/39; A23L 33/10; A23L 33/105; A23L 33/135; A23L 33/14; A23V 2002/00

See application file for complete search history.

*Primary Examiner* — Kade Ariani

(57) ABSTRACT

A traditional Chinese medicine fermented preparation for preventing and treating gout is prepared by combining a traditional Chinese medicine formula with probiotics. The traditional Chinese medicine formula includes a certain proportion of *Aconitum carmichaeli, Cinnamomum cassia, Ephedra sinica, Atractylodes lancea, Saposhnikovia divaricate, Smilax glabra, Paeonia lactiflora, Anemarrhena asphodeloides, Coix lacryma-jobi*, gypsum, and *Glycyrrhiza uralensis*. The probiotics includes *Lactobacillus plantarum, Lactobacillus acidophilus, Lactobacillus casei, Lactobacillus rhamnosus* and yeast. Drug bioavailability is improved by fermentation, maximizing therapeutic effects. A combination application of different probiotics plays a very important role in regulating and optimizing intestinal microbiota of a body, making clinical treatment of the gout more effective.

9 Claims, 1 Drawing Sheet

TRADITIONAL CHINESE MEDICINE FERMENTED PREPARATION FOR PREVENTING AND TREATING GOUT, ITS PREPARATION METHOD AND APPLICATION

CROSS-REFERENCE TO RELATED APPLICATION

This application claims priority to Chinese Patent Application No. 202310697717.5, filed Jun. 13, 2023, which is herein incorporated by reference in its entirety.

TECHNICAL FIELD

The disclosure relates to the field of probiotic fermentation technologies in traditional Chinese medicine, and more particularly to a traditional Chinese medicine fermented preparation for preventing and treating gout, its preparation method and application.

BACKGROUND

Gout is a crystal related joint disease caused by deposition of monosodium urate salts, and directly related to hyperuricemia caused by purine metabolism disorders and/or decreased uric acid excretion. The gout specifically refers to acute characteristic arthritis and chronic tophaccous gout, mainly including acute paroxysmal arthritis, gout tophi formation, chronic tophaccous arthritis, urate nephropathy, and uric acid urinary tract stones. In severe cases, joint deformity and renal dysfunction may occur.

The incidence of gout is relatively high, especially in coastal areas. According to relevant data, the gout incidence in China is 13.3%, while as high as 20%~25% in Japan. The gout incidence continues to rise and tends to be younger, causing a huge burden on public health and society, and the gout becomes a second largest metabolic disease threatening human health. At present, drugs used in clinical practice to treat the gout and hyperuricemia are mainly allopurinol, benzbromarone and probenecid etc. Although the drugs achieve certain therapeutic effects, side effects of the drugs are obvious and affect life quality of patients. In recent years, traditional Chinese medicine has obvious advantages in preventing and treating the gout: firstly, the traditional Chinese medicine emphasizes a holistic concept and dialectical medication; secondly, traditional Chinese medicine formulas have obvious effects and fewer side effects; thirdly, prices of Chinese herbal medicine are reasonable and an acceptance rate of patients is high. In recent years, research confirms that the traditional Chinese medicine has features of multiple pathways, multiple levels, and multiple targets in treating the gout, and its therapeutic effects is definite. However, the traditional Chinese medicine has drawbacks such as a cumbersome decoction process, inconvenience of carrying, bad smell and bad taste etc., which limit patient compliance.

With emergence of modern fermentation technology, traditional Chinese medicine extracts are fermented with selected probiotics that overcome the drawbacks of the traditional Chinese medicine prescriptions. It has advantages of a high utilization rate of effective ingredients, good therapeutic effects, good medicine taste, convenient use, and a high patient compliance rate.

SUMMARY

In response to above problems, a first purpose of the disclosure is to provide a traditional Chinese medicine fermented preparation for preventing and treating gout, a second purpose of the disclosure is to provide a preparation method of the traditional Chinese medicine fermented preparation and a third purpose of the disclosure is to provide applications of the traditional Chinese medicine fermented preparation. The disclosure adopts a traditional Chinese medicine fermentation process, which combines an efficient traditional Chinese medicine formula for preventing and treating the gout with selected probiotics. Through fermentation, drug bioavailability is improved, and a preparation effect is significantly improved, thereby effectively preventing and treating the gout.

In order to achieve above purposes, specific solutions of the disclosure are below.

In a first aspect, the traditional Chinese medicine fermented preparation for preventing and treating the gout is prepared by fermenting raw materials of a traditional Chinese medicine formula with probiotics. The raw materials include the following medicinal materials in parts by weight: 10-30 grams (g) of *Aconitum carmichaeli,* 10-20 g of *Cinnamomum cassia,* 6-12 g of *Ephedra sinica,* 16-18 g of *Atractylodes lancea,* 4.5-12 g of *Saposhnikovia divaricate,* 30-60 g of *Smilax glabra,* 15-30 g of *Paeonia lactiflora,* 10-24 g of *Anemarrhena asphodeloides,* 20-60 g of *Coix lacryma-jobi,* 30-60 g of gypsum ($CaSO_4 \cdot 2H_2O$), and 6-12 g of *Glycyrrhiza uralensis*. The probiotics include: *Lactobacillus plantarum, Lactobacillus acidophilus, Lactobacillus casei, Lactobacillus rhamnosus* and yeast.

In a second aspect, the preparation method includes following steps.

(1) 10-20 g of the *Cinnamomum cassia,* 16-18 g of the *Atractylodes lancea,* 4.5-12 g of the *Saposhnikovia divaricate,* 30-60 g of the *Smilax glabra,* 15-30 g of the *Paeonia lactiflora,* 10-24 g of the *Anemarrhena asphodeloides,* 20-60 g of the *Coix lacryma-jobi* and 30-60 g of the gypsum are weighed as a first raw material, the first raw material is pulverized by using ultrafine pulverization technology of traditional Chinese medicine followed by sieving through a 300-mesh sieve to obtain a first ultrafine powder.

(2) 10-30 g of the *Aconitum carmichaeli,* 6-12 g of the *Ephedra sinica* and 6-12 g of the *Glycyrrhiza uralensis* are weighed as a second raw material, the second raw material is similarly pulverized by using the ultrafine pulverization technology followed by sieving through a 300-mesh sieve to obtain a second ultrafine powder.

(3) The first ultrafine powder prepared in the step (1) is mixed with a powder of *Glycine max* as a nitrogen source, glucose as a carbon source, and pure water in a weight ratio of 1:0.3:0.2:10 to obtain a first mixture, the first mixture is decocted at a temperature of 100 degrees Celsius (° C.) for 10 minutes (min) to 120 min followed by cooling to obtain a first cooled mixture, the first cooled mixture is inoculated with 1-5 weight percentage (wt %) of the *Lactobacillus plantarum*, the *Lactobacillus acidophilus* and the *Lactobacillus casei* with an initial pH in a range of 5.5-6.5 at a temperature in a range of 33-35° C. and then fermented for 1-5 days to obtain a first mixed fermentation liquid.

(4) The second ultrafine powder prepared in the step (2) is mixed with peptone as a nitrogen source, glucose as a carbon source and pure water at a weight ratio of 0.2:0.2:0.1:10 to obtain a second mixture, the second mixture is decocted at a temperature of 100° C. for 10 min to 120 min followed by cooling to obtain a second cooled mixture, the second cooled mixture is inoculated with 1-8 wt % of the *Lactobacillus rhamnosus* and the yeast with an initial pH in a range of 7-8 at a temperature in a range of 35-37° C. and then fermented for 1-5 days to obtain a second mixed fermentation liquid.

(5) The first mixed fermentation liquid prepared in the step (3) is mixed with the second mixed fermentation liquid prepared in the step (4) at a volume ratio in a range of 10-15:1 to obtain a traditional Chinese medicine fermented preparation.

In an embodiment, a probiotic content standard in the traditional Chinese medicine fermented preparation is as follows: viable counts of the *Lactobacillus plantarum*, the *Lactobacillus acidophilus* and the *Lactobacillus casei* are in a range of 1.0-5.0×$10^9$ colony-forming units per milliliter (cfu/mL) individually, and viable counts of the *Lactobacillus rhamnosus* and the yeast are in a range of 1.0-5.0×$10^7$ cfu/mL individually.

In an embodiment, a dosage form of the traditional Chinese medicine fermented preparation includes live bacteria oral liquid and solid beverage dosage forms. The traditional Chinese medicine fermented preparation can uses a tablet dosage form after freeze-drying, further to prepare an oral type including granules or capsules and can be in a plaster form or a patch form.

In an embodiment, the traditional Chinese medicine fermented preparation further includes at least one selected from an acidulant, a sweetener, an edible essence and a food-grade flavoring.

In a third aspect, the disclosure provides an application method of the traditional Chinese medicine fermented preparation, the traditional Chinese medicine fermented preparation is applied in preparing drugs for preventing and treating the gout.

In a fourth aspect, the disclosure provides an application method of the traditional Chinese medicine fermented preparation in preparing functional foods, and the functional foods are prepared by combining the traditional Chinese medicine fermented preparation with food or beverages.

Compared to the related art, the disclosure has following advantages and effects.

(1) The traditional Chinese medicine fermented preparation of the disclosure has a better preventive and therapeutic effect than classical prescriptions, and preparation efficacy is significantly enhanced through probiotic fermentation. The traditional Chinese medicine fermented preparation has an inhibitory effect on oxidative stress caused by elevated uric acid levels in a body, and can reduce the oxidative stress in the body during a process of uric acid production by scavenging free radicals, thereby reducing or inhibiting an occurrence of inflammation.

(2) By utilizing modern traditional Chinese medicine fermentation technology, a toxic component of the *Aconitum carmichaeli*, i.e., a bis-ester alkaloid, can be efficiently converted into an effective component, i.e., a mono-ester type alkaloid, achieving synergistic and detoxifying functions of the traditional Chinese medicine, and high medicinal value components, such as glycosides, saponins, organic acid volatile oil, trace elements, polysaccharides, and small peptides etc., in traditional Chinese medicine can overflow, significantly improving an absorption effect of the body.

(3) The disclosure selects a probiotic combination and uses a batched/combined fermentation model of the probiotics to achieve a maximum abundance of the probiotics, significantly improving the drug bioavailability and maximizing the therapeutic effect. Moreover, a combined application of different probiotics plays a very important role in regulating and optimizing the intestinal microbiota of body, making the clinical treatment effect better.

(4) Under the guidance of traditional Chinese medicine theory, the disclosure combines traditional Chinese medicine extracts with preferably selected probiotics and uses the modern Chinese medicine fermentation technology to improve shortcomings of traditional Chinese medicine prescriptions, enhance medicine taste, offer a wide range of dosage forms, and provide convenient use, resulting in high patient compliance.

DETAILED DESCRIPTION OF EMBODIMENTS

Figure 1A:
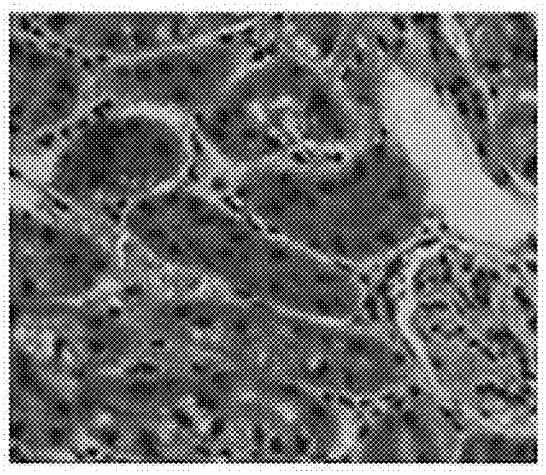
FIG. 1A illustrates a hematoxylin-eosin (HE)-stained section of mouse kidneys in a blank group.

A purpose of the disclosure is to identify a traditional Chinese medicine formula with high efficiency for preventing and treating gout.

The traditional Chinese medicine formula is prepared by the following medicinal materials in parts by weight: 10-30 g of *Aconitum carmichaeli,* 10-20 g of *Cinnamomum cassia,* 6-12 g of *Ephedra sinica,* 16-18 g of *Atractylodes lancea,* 4.5-12 g of *Saposhnikovia divaricate,* 30-60 g of *Smilax glabra,* 15-30 g of *Paeonia lactiflora,* 10-24 g of *Anemarrhena asphodeloides,* 20-60 g of *Coix lacryma-jobi,* 30-60 g of Gypsum ($CaSO_4 \cdot 2H_2O$), and 6-12 g of *Glycyrrhiza uralensis.*

Traditional Chinese medicine considers the gout to fall within a category of Bi (Bi in Chinese means an obstruction) syndrome (i.e., arthralgia syndrome). What is Bi? Shuowen (the first dictionary in China) said that "Bi is a disease caused by dampness." Suwen (a classical text of the traditional Chinese medicine) said that "three evil gas including wind, cold, and dampness invade the body together to cause Bi syndrome. When the evil gas of wind prevails, it is called wind Bi (i.e., wandering arthralgia); when the evil gas of cold prevails, it is called cold Bi (i.e., painful arthralgia); when the evil gas of dampness prevails, it is called dampness Bi (i.e., fixed arthralgia)." The Bi syndrome refers the syndrome characterized by the obstruction of qi and blood in the meridians due to the invasion of external pathogens such as wind, cold, dampness and heat caused by weakness of the body with poor function of defensive qi, manifested as soreness, pain, numbness, heavy sensation, swelling, difficulty in flexing and stretching of muscles, bones and joints, even joint swelling and deformation. The treatment should be based on principles of "eliminating the dampness, dredging the meridians, dispelling the wind, dispersing the cold, alleviating acute symptoms and relieving pain."

The traditional Chinese medicine formula of the disclosure uses the *Aconitum carmichaeli* and the *Cinnamomum cassia* as monarch drugs (also referred to as principal drugs or sovereign drugs, an ingredient that provides a principal curative action on a main pattern/syndrome or primary symptom). The *Aconitum carmichaeli* warms yang (yang qi, a fundamental concept representing warm, active, and energetic aspects of vital life force of the body), dispels the dampness, dissipates the cold and relieves the pain, and the *Cinnamomum cassia* disperses the wind and the cold and warms the meridians. The *Aconitum carmichaeli* and the *Cinnamomum cassia* together disperse both internal and external wind, cold, and dampness pathogens to relieve Bi pain. The *Ephedra sinica* opens interstitial spaces and disperses the cold and the dampness, the *Atractylodes lancea* dries dampness, strengthens a spleen, and disperses the wind and the cold, the *Saposhnikovia divaricata* dispels the wind, overcomes the dampness, and relieves the pain and convulsions, and the *Smilax glabra* detoxifies, dries the dampness, and promotes joint movement. The *Ephedra sinica*, the *Atractylodes lancea*, the *Saposhnikovia divaricata*, and the *Smilax glabra* together serve as minister drugs (an ingredient that helps strengthen the principal curative action), assisting the monarch drugs to disperse the wind, cold, and dampness pathogens and relieve the Bi pain. The *Paeonia lactiflora* nourishes blood (supplementing blood to ensure sufficient blood supply and normal function) and harmonizes blood (making the blood flow smoothly and preventing blood stasis), alleviates the acute symptoms and relieves pain, the *Anemarrhena asphodeloides* nourishes yin (yin qi, representing cold, nourishing, and passive aspects of vital energy of the body) and clears heat, preventing excessively drying effects of pungent-warm medicine, the *Coix lacryma-jobi* induces diuresis to drain the dampness, strengthens the spleen, stops diarrhea, and eliminates Bi, and the gypsum clears heat, purges fire (a more intense form of heat and often related to acute conditions, irritability, and intense inflammation, purging fire means eliminating these extreme heat conditions), relieves irritability and quenches thirst. These four medicines also serve as the assistant and courier, taking their yin nature to assist the yang medicines in the traditional Chinese medicine formula, where yin can help yang and yin can control yang, together achieving the effect of warming yang, dispelling the dampness, relieving the pain, and avoiding the concern of long-term use of warm and dry medicines. The *Glycyrrhiza uralensis* harmonizes all other drugs. The eleven drugs work together to achieve the effect of "dispelling the dampness, dredging the meridians, dispelling the wind, dispersing the cold, alleviating the acute symptoms and relieving the pain."

The disclosure further provides a traditional Chinese medicine fermented preparation for preventing and treating gout and a preparation method thereof. The preparation method includes following steps.

(1) 10-20 g of the *Cinnamomum cassia,* 16-18 g of the *Atractylodes lancea,* 4.5-12 g of the *Saposhnikovia divaricate,* 30-60 g of the *Smilax glabra,* 15-30 g of the *Paeonia lactiflora,* 10-24 g of the *Anemarrhena asphodeloides,* 20-60 g of the *Coix lacryma-jobi* and 30-60 g of the gypsum are weighed as a first raw material, the first raw material is pulverized by using ultrafine pulverization technology of the traditional Chinese medicine, followed by sieving through a 300-mesh sieve to obtain a first ultrafine powder.

(2) 10-30 g of the *Aconitum carmichaeli,* 6-12 g of the *Ephedra sinica* and 6-12 g of the *Glycyrrhiza uralensis* are weighed as a second raw material, the second raw material is pulverized by using the ultrafine pulverization technology followed by sieving through a 300-mesh sieve to obtain a second ultrafine powder.

(3) The first ultrafine powder prepared in the step (1) is mixed with a powder of the *Glycine max* as a nitrogen source, glucose as a carbon source, and pure water in a weight ratio of 1:0.3:0.2:10 to obtain a first mixture, the first mixture is decocted at a temperature of 100° C. for 10-120 min followed by cooling to obtain a first cooled mixture, the first cooled mixture is inoculated with 1-5 wt % of *Lactobacillus plantarum, Lactobacillus acidophilus* and *Lactobacillus casei* with an initial pH in a range of 5.5-6.5 at a temperature in a range of 33-35° C. and then fermented for 1-5 days to obtain the first mixed fermentation liquid.

(4) The second ultrafine powder prepared in the step (2) is mixed with peptone as a nitrogen source, glucose as a carbon source and pure water at a weight ratio of 0.2:0.2:0.1:10 to obtain a second mixture, the second mixture is decocted at a temperature of 100° C. for 10-120 min followed by cooling to obtain a second cooled mixture, the second cooled mixture is inoculated with 1-8 wt % of the *Lactobacillus rhamnosus* and the yeast with an initial pH in a range of 7-8 at a temperature in a range of 35-37° C. and then fermented for 1-5 days to obtain the second mixed fermentation liquid.

(5) The first mixed fermentation liquid prepared in the step (3) is mixed with the second mixed fermentation liquid prepared in the step (4) at a volume ratio in a range of 10-15:1 to obtain the traditional Chinese medicine fermented preparation.

When the traditional Chinese medicine fermented preparation is applied in preventing and treating the gout, a dosage form of the traditional Chinese medicine fermented preparation includes live bacteria oral liquid and solid beverage dosage forms. The traditional Chinese medicine fermented preparation can also use a tablet dosage form after freeze-drying, further to prepare an oral type including granules or capsules and can be in a plaster form, a patch form and other formulations.

A further description of the traditional Chinese medicine compatibility and technical solutions of the disclosure are provided in conjunction with embodiments. However, the content of the disclosure is not limited to the scope described in the embodiments. Any ideas and equivalent substitutions that do not deviate from the disclosure are within the scope of protection of the disclosure.

In the following embodiments, if not specifically mentioned, reagents and materials used in the disclosure are conventional commercially available, and operations used are conventional technical means.

Embodiment 1

A preparation method of the traditional Chinese medicine fermented preparation for preventing and treating the gout includes following steps:

(1) 20 g of the *Cinnamomum cassia,* 18 g of the *Atractylodes lancea,* 12 g of the *Saposhnikovia divaricate,* 60 g of the *Smilax glabra,* 30 g of the *Paeonia lactiflora,* 24 g of the *Anemarrhena asphodeloides,* 60 g of the *Coix lacryma-jobi* and 60 g of the gypsum are weighed as a first raw material, the first raw material is pulverized by using ultrafine pulverization technology of the traditional Chinese medicine followed by sieving through a 300-mesh sieve to obtain a first ultrafine powder.

(2) 30 g of the *Aconitum carmichaeli,* 12 g of the *Ephedra sinica* and 12 g of the *Glycyrrhiza uralensis* are weighed as a second raw material, the second raw material is pulverized by using the ultrafine pulverization technology followed by sieving through a 300-mesh sieve to obtain a second ultrafine powder.

(3) The first ultrafine powder prepared in the step (1) is mixed with a powder of the *Glycine max* (sieved through a 60-mesh sieve) as a nitrogen source, glucose as a carbon source, and pure water in a weight ratio of 1:0.3:0.2:10 to obtain a first mixture, the first mixture is decocted at a temperature of 100° C. for 30 min followed by cooling to obtain a first cooled mixture, the first cooled mixture is inoculated with 1 wt % of the *Lactobacillus plantarum*, the *Lactobacillus acidophilus* and the *Lactobacillus casei* with an initial pH 5.5 at a temperature of 33° C. and then fermented for 5 days to obtain the first mixed fermentation liquid.

(4) The second ultrafine powder prepared in the step (2) is mixed with peptone as a nitrogen source, glucose as a carbon source and pure water at a weight ratio of 0.2:0.2:0.1:10 to obtain a second mixture, the second mixture is decocted at a temperature of 100° C. for 30 min followed by cooling to 37° C. to obtain a second cooled mixture, the second cooled mixture is inoculated with 1 wt % of the *Lactobacillus rhamnosus* and the yeast with an initial pH of 7 at a temperature of 35° C. and then fermented for 5 days to obtain the second mixed fermentation liquid.

(5) The first mixed fermentation liquid prepared in the step (3) is mixed with the second mixed fermentation liquid prepared in the step (4) at a volume ratio of 10:1 to obtain the traditional Chinese medicine fermented preparation.

(6) A probiotic content in the traditional Chinese medicine fermented preparation is as follows: the *Lactobacillus plantarum*, the *Lactobacillus acidophilus* and the *Lactobacillus casei* with viable counts of $1.0\times10^9$ cfu/mL individually, as well as the *Lactobacillus rhamnosus* and the live yeast with viable counts of $1.0\times10^7$ cfu/mL individually.

(7) A preferable dosage form of the traditional Chinese medicine fermented preparation is live bacteria oral liquid, and can also be an oral ointment after concentration.

Embodiment 2

A preparation method of the traditional Chinese medicine fermented preparation for preventing and treating the gout includes following steps:

(1) 10 g of the *Cinnamomum cassia,* 16 g of the *Atractylodes lancea,* 4.5 g of the *Saposhnikovia divaricate,* 30 g of the *Smilax glabra,* 15 g of the *Paeonia lactiflora,* 10 g of the *Anemarrhena asphodeloides,* 20 g of the *Coix lacryma-jobi* and 30 g of the Gypsum are weighed as a first raw material, the first raw material is pulverized by using ultrafine pulverization technology of the traditional Chinese medicine followed by sieving through a 300-mesh sieve to obtain a first ultrafine powder.

(2) 10 g of the *Aconitum carmichaeli,* 6 g of the *Ephedra sinica* and 6 g of the *Glycyrrhiza uralensis* are weighed as a second raw material, the second raw material is pulverized by using the ultrafine pulverization technology followed by sieving through a 300-mesh sieve to obtain a second ultrafine powder.

(3) The first ultrafine powder prepared in the step (1) is mixed with a powder of the *Glycine max* (sieved through a 60-mesh sieve) as a nitrogen source, glucose as a carbon source, and pure water in a weight ratio of 1:0.3:0.2:10 to obtain a first mixture, the first mixture is decocted at a temperature of 100° C. for 120 min followed by cooling to obtain a first cooled mixture, the first cooled mixture is inoculated with 4 wt % of the *Lactobacillus plantarum*, the *Lactobacillus acidophilus* and the *Lactobacillus casei* with an initial pH of 6.5 at a temperature of 35° C. and then fermented for 3 days to obtain the first mixed fermentation liquid.

(4) The second ultrafine powder prepared in the step (2) is mixed with peptone as a nitrogen source, glucose as a carbon source and pure water at a weight ratio of 0.2:0.2:0.1:10 to obtain a second mixture, the second mixture is decocted at a temperature of 100° C. for 120 min followed by cooling to obtain a second cooled mixture, the second cooled mixture is inoculated with 2.5 wt % of the *Lactobacillus rhamnosus* and the yeast with an initial pH of 8 at a temperature of 37° C. and then fermented for 3 days to obtain the second mixed fermentation liquid.

(5) The first mixed fermentation liquid prepared in the step (3) is mixed with the second mixed fermentation liquid prepared in the step (4) at a volume ratio of 15:1 to obtain the traditional Chinese medicine fermented preparation.

(6) A probiotic content in the traditional Chinese medicine fermented preparation is as follows: viable counts of the *Lactobacillus plantarum*, the *Lactobacillus acidophilus* and the *Lactobacillus casei* are $5.0\times10^9$ cfu/mL individually, and viable counts of the *Lactobacillus rhamnosus* and the live yeast are $5.0\times10^7$ cfu/mL individually.

(7) The traditional Chinese medicine fermented preparation preferably uses a tablet dosage form after freeze-drying, or a granule after freeze-drying, or a capsule after freeze-drying.

Embodiment 3

A preparation method of the traditional Chinese medicine fermented preparation for preventing and treating the gout includes following steps:

(1) 15 g of the *Cinnamomum cassia,* 15 g of the *Atractylodes lancea,* 10 g of the *Saposhnikovia divaricate,* 30 g of the *Smilax glabra,* 24 g of the *Paeonia lactiflora,* 15 g of the *Anemarrhena asphodeloides,* 30 g of the *Coix lacryma-jobi* and 45 g of the Gypsum are weighed as a first raw material, the first raw material is pulverized by using ultrafine pulverization technology of the traditional Chinese medicine followed by sieving through a 300-mesh sieve to obtain a first ultrafine powder.

(2) 15 g of the *Aconitum carmichaeli,* 10 g of the *Ephedra sinica* and 8 g of the *Glycyrrhiza uralensis* are weighed as a second raw material, the second raw material is pulverized by using the ultrafine pulverization technology followed by sieving through a 300-mesh sieve to obtain a second ultrafine powder.

(3) The first ultrafine powder prepared in the step (1) is mixed with a powder of the *Glycine max* (sieved through a 60-mesh sieve) as a nitrogen source, glucose as a carbon source, and pure water in a weight ratio of 1:0.3:0.2:10 to obtain a first mixture, the first mixture is decocted at a temperature of 100° C. for 60 min followed by cooling to obtain a first cooled mixture, the first cooled mixture is inoculated with 8 wt % of the *Lactobacillus plantarum*, the *Lactobacillus acidophilus* and the *Lactobacillus casei* with an initial pH of 6 at a temperature of 34° C. and then fermented for 48 h to obtain a first mixed fermentation liquid.

(4) The second ultrafine powder prepared in the step (2) is mixed with peptone as a nitrogen source, glucose as a carbon source and pure water at a weight ratio of 0.2:0.2:0.1:10 to obtain a second mixture, the second mixture is decocted at a temperature of 100° C. for 60 min followed by cooling to obtain a second cooled mixture, the second cooled mixture is inoculated with 5 wt % of the *Lactobacillus rhamnosus* and the yeast with an initial pH of 8 at a temperature of 36° C. and then fermented for 48 h to obtain a second mixed fermentation liquid.

(5) The first mixed fermentation liquid prepared in the step (3) is mixed with the second mixed fermentation liquid prepared in the step (4) at a volume ratio of 13:1 to obtain a traditional Chinese medicine fermented preparation.

(6) A probiotic content in the traditional Chinese medicine fermented preparation is as follows: viable counts of the *Lactobacillus plantarum*, the *Lactobacillus acidophilus* and the *Lactobacillus casei* are $2.5\times10^9$ cfu/mL individually, and viable counts of the *Lactobacillus rhamnosus* and the live yeast are $2.5\times10^7$ cfu/mL individually.

(7) The traditional Chinese medicine fermented preparation is prepared into a paste and patch form by low-temperature concentration, and applied to an inflamed area when in use.

Embodiment 4: Comparison of Effective Ingredient Content Between Ultrafine Powder and Conventional Powder of Raw Gypsum A main component of the gypsum is calcium sulfate dihydrate ($CaSO_4 \cdot 2H_2O$), which has effects of clearing heat and purging fire, relieving irritability and quenching thirst. However, solubility of the gypsum in decoctions is very low. To improve the solubility of the gypsum, decocted-first and pulverization are adopted in clinical practices, which improve efficacy to varying degrees. The disclosure uses ultrafine pulverization technology to produce ultrafine gypsum powder to further enhance the efficacy. The disclosure uses an ultrafine traditional Chinese medicine pulverizer (300 mesh) and a regular pulverizer (60-80 mesh) for pulverization, and samples are then taken to test the content of the $CaSO_4 \cdot 2H_2O$. The testing method follows a pharmacopoeia method for testing the $CaSO_4 \cdot 2H_2O$ in the gypsum, using spectrophotometry and barium sulfate ($BaSO_4$) weight method for detection. Test results show that an average content of the $CaSO_4 \cdot 2H_2O$ in the gypsum after ultrafine pulverization is 91.21% by the spectrophotometry and 92.01% by the barium sulfate weight method, while the average content of the $CaSO_4 \cdot 2H_2O$ in the gypsum after regular pulverization is 67.50% by the spectrophotometry and 68.23% by the barium sulfate weight method. Therefore, a utilization rate of the Chinese traditional medicine is higher after ultrafine pulverization, and the effective components of the Chinese traditional medicine can be more readily dissolved and released (Table 1).

TABLE 1

Comparison of the $CaSO_4 \bullet 2H_2O$ content in the gypsum by the ultrafine pulverization technology and the regular pulverization.

| | $CaSO_4 \bullet 2H_2O$ content | |
|---|---|---|
| Group | Spectro-photometry | Barium sulfate weight method |
| Gypsum powder after ultrafine pulverization | 91.27% | 92.01% |
| Gypsum powder after regular pulverization | 67.50% | 68.23% |

Embodiment 5: Comparison of Toxic Component Content Between Traditional Decoction and Fermented Preparation in Preparation of the *Aconitum carmichaeli*

Bis-ester alkaloids and mono-ester alkaloids in the *Aconitum carmichaeli* are both toxic and effective components. Bis-ester alkaloids have effects such as analgesic and anesthetic etc., but are highly toxic with a narrow therapeutic window. However, the mono-ester alkaloids, which are formed by deacetylation of the bis-ester alkaloids, have similar pharmacological activities but are significantly less toxic, with toxicity being 1/64-1/180 of the bis-ester alkaloids, offering a relatively wider safe therapeutic range. The disclosure utilizes modern fermentation technology of Chinese traditional medicine to process the *Aconitum carmichaeli*, promoting transformation of the bis-ester alkaloids with high toxicity into the mono-ester alkaloids with gentle therapeutic effects. The *Aconitum carmichaeli* prepared in a same batch are used as experimental subjects, samples are taken and tested for contents of the mono-ester and the bis-ester alkaloids by different methods: sand-pot decoction, machine decoction, and microbial fermentation. The testing method employs high-performance liquid chromatography (HPLC) to measure the contents of the mono-ester and the bis-ester alkaloids in the *Aconitum carmichaeli.*

The sand-pot decoction specifically includes: water with an amount 10 times the weight of the *Aconitum carmichaeli* is added to the *Aconitum carmichaeli*, and the *Aconitum carmichaeli* is soaked for 60 min and then decocted for 1 h followed by filtering to obtain a first filtrate and a first residue, the first residue is added with water with an amount 10 times the weight of the first residue and then decocted for 1 h followed by filtering to obtain a second filtrate, the first filtrate is added to the second filtrate to obtain a sand-pot decoction sample.

The machine decoction specifically includes: water with an amount 10 times the weight of the *Aconitum carmichaeli* is added to the *Aconitum carmichaeli*, and the *Aconitum carmichaeli* is soaked for 60 min and then decocted over a gentle heat for 1 h followed by filtering to obtain a third filtrate and a second residue, the second residue is added with water with an amount 10 times the weight of the second residue and then decocted over a gentle heat for 1 h followed by filtering to obtain a fourth filtrate, the third filtrate is added to the fourth filtrate to obtain a machine decoction sample.

The fermentation liquid of the *Aconitum carmichaeli* method specifically includes: the *Aconitum carmichaeli*, the *Ephedra sinica* and the *Glycyrrhiza uralensis* are weighed, pulverized, and sieved through a 300-mesh sieve to obtain an ultrafine powder. The ultrafine powder is mixed with peptone as a nitrogen source, glucose as a carbon source and pure water at a weight ratio of 0.2:0.2:0.1:10 to obtain a mixture, the mixture is decocted and sterilized at a temperature of 100° C. for 1 h followed by cooling to obtain a cooled mixture, 2.5 wt % of the *Lactobacillus rhamnosus* and the yeast is inoculated with the cooled mixture, followed fermenting for 48 h with an initial pH of 8 at a temperature of 36° C. to obtain a fermented mixture. The fermented mixture is filtered for solid-liquid separation to obtain the fermentation liquid of the *Aconitum carmichaeli.*

Test results show that the content of the mono-ester alkaloids in the *Aconitum carmichaeli* with the microbial fermentation is 0.0223%, which is an increase of 47.68% compared to that in the sand-pot decoction, and an increase of 36.73% compared to that in the machine decoction. The content of the bis-ester alkaloids in the *Aconitum carmichaeli* with the microbial fermentation is 0.0041%, which is a reduction of 50.60% compared to that in the sand-pot decoction, and a reduction of 48.34% compared to that in the machine decoction.

(Table 2)

TABLE 2

Comparison of the toxic component content between the traditional decoction and the fermented preparation in the preparation of the *Aconitum carmichaeli*.

| Method | Content of mono-ester alkaloids | Content of bis-ester alkaloids |
|---|---|---|
| Sand-pot decoction | 0.0117% | 0.0062% |
| Machine decoction | 0.0110% | 0.0061% |
| Fermentation liquid | 0.0223% | 0.0041% |

Figure 1B:
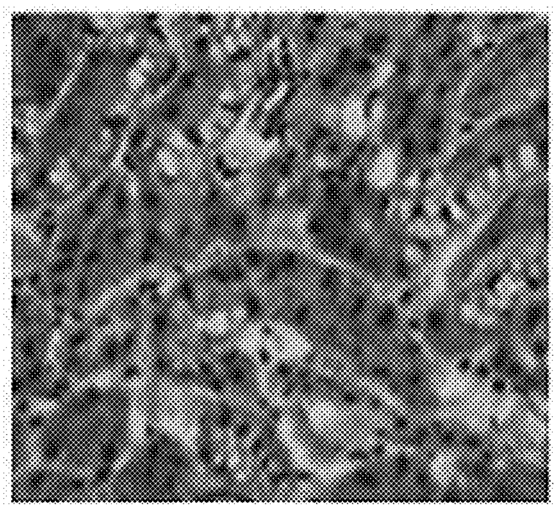
FIG. 1B illustrates a HE-stained section of mouse kidneys in a control group.
Figure 1C:
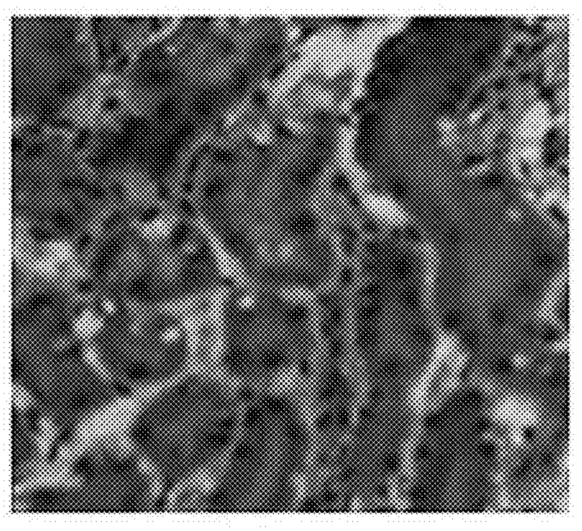
FIG. 1C illustrates a HE-stained section of mouse kidneys in a treated group.

Embodiment 6: Toxicity Experiment of the Traditional Chinese Medicine Fermented Preparation 60 mice (each mouse with a weight of (20±2) g) are taken and randomly divided into 3 groups, with 20 mice in each group, denoted as a treated group, a control group and a blank group respectively. The mice in the treated group are administrated with the traditional Chinese medicine fermented preparation of the disclosure at a dosage of 1 milliliter per kilogram (mL/kg), twice a day via gavage. The mice in the control group are given physiological saline at a dosage of 1 mL/kg, twice a day via gavage. The mice in the blank group are free to eat and drink. After 30 days, mental states, feeding, drinking, and other behaviors of the mice in each group are observed. It is found that the mice in the treated group and the control group have glossy fur, normal diet, normal activity, and normal excrement, with no abnormal secretions from noses, eyes, or mouths, and no deaths, the mice in the treated group and the control group show no significant differences compared to the mice in the blank group. Upon autopsy, HE staining results of mouse kidneys show that, compared to the blank group, kidney tissues of the mice in other two groups show no signs of renal tubular dilation, inflammatory infiltration, necrosis, or shedding of renal tubular epithelial cells, indicating no obvious damage to renal structure (FIG. 1A to FIG. 1C). The experiment proves that there is no significant difference between the treated group and the control group and the blank group, and no toxic reaction is observed, indicating that the traditional Chinese medicine fermented preparation is safe.

Embodiment 7: Effect on Serum Uric Acid (UA) Levels in Mice with Hyperuricemia 60 mice (each mouse with a weight of (20±2) g) are taken and randomly divided into 6 groups, with 10 mice in each group, denoted as a blank group, a model group, a benzbromarone group, a high dose traditional Chinese medicine fermented preparation group, a medium dose traditional Chinese medicine fermented preparation group, and a low dose traditional Chinese medicine fermented preparation group. After 5 days of adaptive breeding, except for the blank group (injected with an equal volume of physiological saline), the mice in other groups are injected intraperitoneally with 0.3 g/kg/mouse of hypoxanthine+0.05 g/kg/mouse of potassium oxonate (i.e., oxonic acid potassium salt) daily for model replication, for 7 consecutive days. At the same time, the mice in the benzbromarone group are administered orally at a dose of 0.02 g/kg/mouse once a day, the mice in the high, medium and low dose traditional Chinese medicine fermented preparation groups are administered orally at a dose of 2 mL/kg/mouse, 1 mL/kg/mouse, and 0.5 mL/kg/mouse once, respectively, while the mice in the blank group and the model group are given physiological saline (1 mL/kg) orally, for 7 consecutive days. After 7 days, tail vein blood is collected from the mice in all groups, and then centrifuged to separate plasma to obtain serum, the serum is taken to measure serum UA levels. Results show that compared to the blank group, the serum UA level of the mice in the model group is significantly increased ($P<0.01$). Compared to the model group, the serum UA levels of the mice in the treated group are significantly reduced ($P<0.01$). It indicates that the traditional Chinese medicine fermented preparation can significantly reduce the serum UA levels in mice with hyperuricemia (Table 3).

TABLE 3

The effect of traditional Chinese medicine fermentation preparation on the serum UA levels in the mice with hyperuricemia.

| Groups | Dose (g/kg or mL · kg) | Serum UA level/μmol/L |
|---|---|---|
| Blank group | — | 145.80 |
| Model group | — | 768.30 |
| Benzbromarone group | 0.02 | 302.30 |
| High dose traditional Chinese medicine fermented preparation group | 0.33 | 297.00 |
| Medium dose traditional Chinese medicine fermented preparation group | 0.67 | 341.20 |
| Low dose traditional Chinese medicine fermented preparation group | 1.33 | 417.70 |

Embodiment 8: Efficacy Comparison Between the Traditional Chinese Medicine Fermented Preparation of the Disclosure and a Classical Prescription for Treating Acute Gouty Arthritis 40 gouty patients are randomly selected from outpatient clinics, excluding those under 18 years old or over 65 years old, secondary gout caused by kidney disease, medication, tumor chemotherapy or radiotherapy, drug allergies, gouty nephropathy, renal insufficiency, and those with serious primary diseases of the heart, liver, kidney, brain, and hematopoietic system, as well as mental illness. The 40 gouty patients are randomly divided into 2 groups, an experimental group with 20 gouty patients and a control group with 20 gouty patients. There are no significant differences in age, gender, clinical manifestations, and other aspects between the two groups after statistical analysis ($P>0.05$).

Diagnostic criteria are below: (1) Serum UA levels in a range of 420 to 520 micromole per liter (μmol/L), (2) specific urate crystals in joint fluid; (3) acute arthritis attack within 24 hours (intense pain in tan affected joint, manifested as redness, swelling, heat, and pain, accompanied by symptoms such as general malaise), and (4) negative microbial culture of joint fluid during the arthritis attack onset.

The gouty patients in the experimental group take the traditional Chinese medicine fermented preparation of the disclosure, twice a day with one dose per time. A 10-day period is one course of treatment, and the treatment is continued for two courses consecutively. The gouty patients in the control group take the classical prescription: 10 parts of the *Cinnamomum cassia,* 30 parts of the *Paeonia lactiflora,* 15 parts of the *Anemarrhena asphodeloides,* 12 parts of *Atractylodes macrocephala* (fried), 10 parts of the *Aconitum carmichaeli* (decocted-first), 15 parts of the *Saposhnikovia divaricata,* 6 parts of the *Ephedra sinica,* 40 parts of the gypsum (decocted-first), 60 parts of *Pueraria lobata,* 10 parts of *Angelica pubescens* f, biserrata, 9 parts of *Zingiber officinale*, and 6 parts of the *Glycyrrhiza uralensis* are decocted in water and taken in two divided doses per day. A 10-day period is one course of treatment, and the treatment is continued for two courses consecutively. During the treatment, clinical symptoms of the gouty patients in the two groups are monitored, including joint swelling index, joint pain index, and joint dysfunction index; after the treatment, laboratory indicators such as serum UA, C-reactive protein, and erythrocyte sedimentation rate are tested. Total efficacy of the treatment in both two groups is compared according to the following standards. Total efficacy rate=(marked effect+effective)/total number of cases×100%.

Marked effect: the clinical symptoms of the gouty patients are significantly improved, laboratory test indicators show a clear improvement, and daily life is not affected. Effective: the clinical symptoms of the gouty patients are improved, and the gouty patients can perform light labor daily activities, laboratory indicators are improved to some extent. Ineffective: the clinical symptoms of the gouty patients do not change compared to before the treatment, and even patient condition gets worsened. Results of the clinical symptoms show: data of the experimental group and the control group before the treatment are not statistically significant (P>0.05), after treatment, data of the experimental group are all better than those of the control group, and there is a statistically significant difference between the two groups (P<0.05). Although both two groups show good prevention and treatment effects, the experimental group treated with the traditional Chinese medicine fermented preparation shows a significant improvement compared to the control group treated with the classical prescription (Table 4).

TABLE 4

Clinical symptom improvement comparison between the traditional Chinese medicine fermented preparation of the disclosure and the classical prescription for treating acute gouty arthritis.

| Groups | Cases | Time | joint swelling index | joint pain index | joint dysfunction index |
|---|---|---|---|---|---|
| Experimental group | 20 | Before treatment | 14.06 | 15.29 | 2.45 |
| | 20 | After treatment | 4.46 | 4.31 | 0.68 |
| Control group | 20 | Before treatment | 14.17 | 14.87 | 2.61 |
| | 20 | After treatment | 6.31 | 7.13 | 1.41 |

Laboratory indicator results show: There is no statistical significance in the data between the experimental group and the control group before the treatment (P>0.05). After the treatment, the data of the observation group are all lower than those of the control group, and the difference in data comparison has statistical significance (P<0.05). As shown in Table 5, after the treatment with the two groups, there are significant changes in the laboratory test indicators of the experimental group and the control group, with the effect of the experimental group being more pronounced.

TABLE 5

Laboratory test indicators comparison between the experimental group and the control group

| Groups | Cases | Time | Serum UA (μmol/L) | C-reactive protein (mm/h) | Erythrocyte sedimentation (mg/L) |
|---|---|---|---|---|---|
| Experimental group | 20 | Before treatment | 457 | 30.36 | 21.43 |
| | 20 | After treatment | 233 | 12.15 | 7.21 |
| Control group | 20 | Before treatment | 456 | 30.95 | 22.86 |
| | 20 | After treatment | 335 | 24.97 | 12.95 |

Clinical efficacy comparison results show: treatment efficiency of the experimental group is higher than that of the control group (P<0.05). Through comparison of clinical treatment effects, both the classical prescription of the control group and the traditional Chinese medicine fermented preparation of the experimental group have good therapeutic effects on gouty arthritis, and the effects of the experimental group are more pronounced, which has significant application value (Table 6).

TABLE 6 efficacy comparison between the experimental group and the control group.

| Groups | Cases | Marked effect | Effective | Ineffective | Total efficacy |
|---|---|---|---|---|---|
| Experimental group | 20 | 12 (60%) | 7 (35%) | 1 (5%) | 95% |
| Control group | 20 | 9 (45%) | 7 (35%) | 4 (20%) | 80% |

Typical cases are below:

Case 1: Zhang, male, 38 years old, from Zhengzhou, Henan, China. In May 2020, he suddenly experienced severe pain, swelling, redness, and heat in the right big toe, with a slightly dark purple-black color and unbearable pain. He is diagnosed with gout at the First Affiliated Hospital of Henan University of Science and Technology in Luoyang, with a serum UA level as high as 480 μmol/L. After 4 months of western medicine treatment with no significant effect, he starts taking the traditional Chinese medicine fermented preparation of the embodiment 1, with 100 mL each time, twice a day, after breakfast and dinner. A 5-day period is a treatment course, and after two consecutive courses, the pain was significantly reduced. After continuing for 10 days, symptoms basically disappeared, the serum UA level dropped to 318 μmol/L, and there has been no recurrence to date.

Case 2: Qian, male, 53 years old, from Jimo, Qingdao, China. The patient had suffered from gout for 12 years, with redness and pain in his right foot, gradually developing to the point of being unable to walk. He had sought treatment in various major hospitals in Beijing and provinces with poor results, suffering from annual recurrences and spending tens of thousands of yuan on treatment. When he was admitted in July 2020, his right foot was swollen, he couldn't wear shoes, and he had stabbing pain in the interphalangeal joint of the big toe, making it impossible to walk. He started taking the traditional Chinese medicine fermented preparation of the embodiment 1, with 100 mL each time, twice a day, after breakfast and dinner. A 5-day period is a treatment course, and after two courses, his condition improved, he can wear shoes and walk normally, and the serum UA level dropped to 324 μmol/L. He continued with two courses, symptoms basically disappeared, and there has been no recurrence upon follow-up.

Finally, it should be noted that the above embodiments are only used to illustrate the technical solution of the disclosure, and not to limit. Although the disclosure is described in detail with reference to the embodiments, those skilled in the art should understand that they can still modify the technical solutions recorded in the embodiments or equivalently replace some of the technical features thereof. And these modifications or replacements do not make the essence of the corresponding technical solutions deviate from the scope of the technical solutions of the various embodiments of the disclosure.

What is claimed is:

1. A traditional Chinese medicine fermented preparation for preventing and treating gout, prepared by fermenting raw materials of a traditional Chinese medicine formula with probiotics;

wherein the raw materials comprise the following medicinal materials in parts by weight: 10 grams (g)-30 g of *Aconitum carmichaelii,* 10 g-20 g of *Cinnamomum cassia,* 6 g-12 g of *Ephedra sinica,* 16 g-18 g of *Atractylodes lancea,* 4.5 g-12 g of *Saposhnikovia divaricata,* 30 g-60 g of *Smilax glabra,* 15 g-30 g of *Paeonia lactiflora,* 10 g-24 g of *Anemarrhena asphodeloides,* 20 g-60 g of *Coix lacryma-jobi,* 30 g-60 g of gypsum ($CaSO_4 \cdot 2H_2O$), and 6 g-12 g of *Glycyrrhiza uralensis;* wherein the probiotics comprise: *Lactobacillus plantarum, Lactobacillus acidophilus, Lactobacillus casei, Lactobacillus rhamnosus* and yeast.

2. A preparation method of the traditional Chinese medicine fermented preparation as claimed in claim 1, comprising following steps:

(1) weighing 10 g-20 g of the *Cinnamomum cassia,* 16 g-18 g of the *Atractylodes lancea,* 4.5 g-12 g of the *Saposhnikovia divaricata,* 30 g-60 g of the *Smilax glabra,* 15 g-30 g of the *Paeonia lactiflora,* 10 g-24 g of the *Anemarrhena asphodeloides,* 20 g-60 g of the *Coix lacryma-jobi* and 30 g-60 g of the gypsum as a first raw material, then pulverizing the first raw material by using a ultrafine pulverization technology of traditional Chinese medicine, followed by sieving through a 300-mesh sieve to obtain a first ultrafine powder;

(2) weighing 10 g-30 g of the *Aconitum carmichaelii,* 6 g-12 g of the *Ephedra sinica* and 6 g-12 g of the *Glycyrrhiza uralensis* as a second raw material, then pulverizing the second raw material by using the ultrafine pulverization technology, followed by sieving through a 300-mesh sieve to obtain a second ultrafine powder;

(3) mixing the first ultrafine powder prepared in the step (1) with a powder of *Glycine max* as a nitrogen source, glucose as a carbon source, and pure water in a weight ratio of 1:0.3:0.2:10 to obtain a first mixture, decocting the first mixture at a temperature of 100 degrees Celsius (C) for 10 minutes (min) to 120 min followed by cooling to obtain a first cooled mixture, inoculating the first cooled mixture with 1-5 weight percentage (wt %) of the *Lactobacillus plantarum*, the *Lactobacillus acidophilus* and the *Lactobacillus casei* with an initial pH in a range of 5.5-6.5 at a temperature in a range of 33° C.-35° C. and then fermenting for 1-5 days to obtain first mixed fermentation liquid;

(4) mixing the second ultrafine powder prepared in the step (2) with peptone as a nitrogen source, glucose as a carbon source and pure water at a weight ratio of 0.2:0.2:0.1:10 to obtain a second mixture, decocting the second mixture at a temperature of 100° C. for 10 min to 120 min followed by cooling to obtain a second cooled mixture, inoculating the second cooled mixture with 1-8 wt % of the *Lactobacillus rhamnosus* and the yeast with an initial pH in a range of 7-8 at a temperature in a range of 35° C.-37° C. and fermenting for 1-5 days to obtain second mixed fermentation liquid;

(5) mixing the first mixed fermentation liquid prepared in the step (3) with the second mixed fermentation liquid prepared in the step (4) at a volume ratio in a range of 10-15:1 to obtain the traditional Chinese medicine fermented preparation.

3. The preparation method as claimed in claim 2, wherein a probiotic content standard in the traditional Chinese medicine fermented preparation is as follows: viable counts of the *Lactobacillus plantarum*, the *Lactobacillus acidophilus* and the *Lactobacillus casei* are in a range of $1.0\text{-}5.0\times10^9$ colony-forming units per milliliter (cfu/mL) individually, and viable counts of the *Lactobacillus rhamnosus* and the yeast are in a range of $1.0\text{-}5.0\times10^7$ cfu/mL individually.

4. The preparation method as claimed in claim 2, wherein a dosage form of the traditional Chinese medicine fermented preparation comprises live bacteria oral liquid and solid beverage dosage forms.

5. The preparation method as claimed in claim 2, wherein the traditional Chinese medicine fermented preparation uses a tablet dosage form after freeze-drying, further to prepare an oral type comprising granules or capsules.

6. The preparation method as claimed in claim 2, wherein the traditional Chinese medicine fermented preparation is in a plaster form or a patch form.

7. The preparation method as claimed in claim 2, wherein the traditional Chinese medicine fermented preparation further comprises at least one selected from an acidulant, a sweetener, and food-grade flavoring.

8. A method for treating gout, comprising administering the traditional Chinese medicine fermented preparation as claimed in claim 1 to a subject in need thereof.

9. A method for preparing a function food, comprising combining the traditional Chinese medicine fermented preparation as claimed in claim 1 with a food or a beverage.

* * * * *